United States Patent [19]

Brumby et al.

[11] Patent Number: 5,037,832
[45] Date of Patent: Aug. 6, 1991

[54] 2-SUBSTITUTED ERGOLINES

[75] Inventors: Thomas Brumby; Gerhard Sauer; Josef Heindl; Jonathan Turner; Gerhard Kühne; Helmut Wachtel, all of Berlin, Fed. Rep. of Germany

[73] Assignee: Schering Aktiengesellschaft, Berlin and Bergkamen, Fed. Rep. of Germany

[21] Appl. No.: 380,352

[22] Filed: Jul. 17, 1989

[30] Foreign Application Priority Data

Jul. 15, 1988 [DE] Fed. Rep. of Germany ....... 3824661
May 23, 1989 [DE] Fed. Rep. of Germany ....... 3917268

[51] Int. Cl.$^5$ ................ A61K 31/48; C07D 457/04
[52] U.S. Cl. ........................................ 514/288; 546/68
[58] Field of Search ...................... 546/68; 514/288

[56] References Cited

U.S. PATENT DOCUMENTS

| 4,690,929 | 9/1987 | Bernardi et al. | 546/68 |
| 4,731,367 | 3/1988 | Sauer et al. | 546/68 |
| 4,740,509 | 4/1988 | Sauer et al. | 514/288 |
| 4,766,128 | 8/1988 | Sauer et al. | 514/288 |
| 4,791,115 | 12/1988 | Haefliger | 514/288 |
| 4,826,851 | 5/1989 | Huth et al. | 546/68 |
| 4,826,852 | 5/1989 | Haffer et al. | 546/68 |
| 4,847,262 | 7/1989 | Sauer et al. | 546/68 |
| 4,863,929 | 9/1989 | Sauer et al. | 546/68 |
| 4,874,768 | 10/1989 | Huth et al. | 546/68 |

FOREIGN PATENT DOCUMENTS

| 82808 | 6/1983 | European Pat. Off. | 546/68 |
| 118848 | 9/1984 | European Pat. Off. | 546/68 |
| 126968 | 12/1984 | European Pat. Off. | 546/68 |
| 0160842 | 11/1985 | European Pat. Off. | |
| 160842 | 11/1985 | European Pat. Off. | 546/68 |
| 0250357 | 12/1987 | European Pat. Off. | |
| 3411981 | 10/1985 | Fed. Rep. of Germany | 546/68 |
| 3413659 | 10/1985 | Fed. Rep. of Germany | 546/68 |
| 3533675 | 3/1987 | Fed. Rep. of Germany | 546/68 |
| 3620293 | 12/1987 | Fed. Rep. of Germany | 546/68 |
| 3623437 | 1/1988 | Fed. Rep. of Germany | 546/68 |
| 3623438 | 1/1988 | Fed. Rep. of Germany | 546/68 |
| 2185743 | 7/1987 | United Kingdom | 546/68 |

OTHER PUBLICATIONS

Sauer et al, Chem. Abst. 105-43138e, 105-43139f (1986).
Sauer et al., Chem. Abst. 109-6778a (1988).

Primary Examiner—Cecilia Shen
Attorney, Agent, or Firm—Millen, White & Zelano

[57] ABSTRACT

2-Substituted ergolines

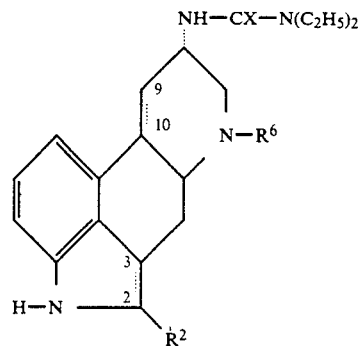

wherein
$C_2\text{---}C_3$ and $C_9\text{---}C_{10}$ represent a single or double bond;
X is oxygen or sulfur;
$R^2$ is $C_{1-10}$ alkyl, optionally halogen-substituted $C_{2-10}$ alkenyl, $CH_2YR^3$, $CR^{12}(OR^4)R^5$, $CH_2\text{-}CHR^9\text{-}COR^{10}$ or $COR^{12}$, wherein
Y is oxygen or sulfur,
$R^3$ is hydrogen, $C_{1-4}$ alkyl, phenyl, $C_{2-5}$ acyl or phenyl $C_{1-4}$ alkyl,
$R^4$ is hydrogen or $C_{2-5}$ acyl,
$R^5$ is $C_{1-9}$ alkyl,
$R^9$ is $COCH_3$ or $COO\text{-}C_{1-4}$ alkyl,
$R^{10}$ is $C_{1-4}$ alkyl or $O\text{-}C_{1-4}$ alkyl,
$R^{12}$ is hydrogen or $C_{1-9}$ alkyl; and
$R^6$ is $C_{2-10}$ alkyl, $C_{3-10}$ alkenyl or $C_{4-10}$ cycloalkyl-$C_{1-3}$-alkyl, and acid addition salts, isomers and isomeric mixtures thereof are dopaminergic agonists and useful for treating Parkinson's Disease.

27 Claims, No Drawings

2-SUBSTITUTED ERGOLINES

BACKGROUND OF THE INVENTION

The invention relates to 2-substituted ergolinylurea derivatives, their production and their use as pharmaceutical agents as well as intermediate products for their production.

2-Substituted ergolinylurea derivatives are known from EP-A-160 842 and EP-A-250 357, and because of their apomorphine-antagonistic effectiveness and/or their $\alpha_2$ receptor-blocking action, the prior art 2-substituted derivatives are particularly suitable as neuroleptic agents.

SUMMARY OF THE INVENTION

It has now been surprisingly found that with the introduction of a long-chain hydrocarbon radical in the 6-position on the 2-substituted ergolinylurea derivatives, the action of dopamine antagonism is shifted to dopamine agonism, and at the same time the metabolic stability of the compounds is retained or improved.

Thus it is an object of the present invention to provide compounds of general formula I

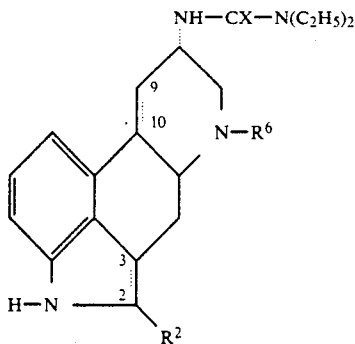

in which
$C_2$—$C_3$ and $C_9$—$C_{10}$ each represent a single or double bond;
X is oxygen or sulfur;
$R^2$ is $C_{1-10}$ alkyl, $C_{2-10}$ alkenyl, halogen-substituted $C_{2-10}$ alkenyl, $CH_2YR^3$, $CR^{12}(OR^4)R^5$, $CH_2$—$CH$—$R^9$—$COR^{10}$ or $COR^{12}$, wherein
Y is oxygen or sulfur,
$R^3$ is hydrogen, $C_{1-4}$ alkyl, phenyl, $C_{2-5}$ acyl or phenyl $C_{1-4}$ alkyl,
$R^4$ is hydrogen or $C_{2-5}$ acyl,
$R^5$ is $C_{1-9}$ alkyl,
$R^9$ is $COCH_3$ or $COO$—$C_{1-4}$ alkyl,
$R^{10}$ is $C_{1-4}$ alkyl or $O$—$C_{1-4}$ alkyl,
$R^{12}$ is hydrogen or $C_{1-9}$ alkyl; and
$R^6$ is $C_{2-10}$ alkyl, $C_{3-10}$ alkenyl or $C_{3-7}$ cycloalkyl-$C_{1-3}$ alkyl, as well as their acid addition salts, isomers and isomeric mixtures.

If $C_9$—$C_{10}$ represents a single bond, the hydrogen atom in the 10-position is in the $\alpha$-position, if $C_2$—$C_3$ represents a single bond, the hydrogen atom in the 3-position is in the $\beta$-position. The compounds of formula I can occur as E or Z isomers or, if a chiral center is present in the radical $R^2$, as diastereomers and as their mixtures.

Suitable alkyl groups in each case are straight-chain or branched alkyl radicals, such as, for example, methyl, ethyl, propyl, isopropyl, butyl, isobutyl, secbutyl, tert-butyl, pentyl, hexyl, heptyl, octyl, nonyl, decyl, 1,2-dimethylheptyl, decyl, 2,2-dimethylpropyl, 2-methylbutyl, 3-methylbutyl, etc.

Suitable alkenyl groups in each case are straight-chain or branched alkenyl radicals, for example, vinyl, 1-propenyl, 2-propenyl, 3-methyl-2-propenyl, 1-butenyl, methallyl, etc.

The alkenyl radical $R^2$ can be substituted singly or doubly with halogen, such as fluorine, chlorine, bromine or iodine, and fluorine and chlorine are preferred.

Suitable acyl groups in each case are alkanoyl groups, e.g., aliphatic carboxylic acids, such as, for example, acetic acid, propionic acid, butyric acid, caproic acid and trimethylacetic acid, etc.

If $R^6$ is a cycloalkyalkyl group, a suitable group is, for example, cyclopropylmethyl, cyclopropylethyl, cyclobutylmethyl, cyclobutylethyl, cyclopentylmethyl, cyclohexylmethyl, cycloheptylmethyl, etc.

Alkyl, alkenyl and cycloalkylalkyl with up to 4 carbon atoms are preferred for the radical $R^6$. The radicals $R^5$ and $R^{12}$ together should not exceed 10, preferably 6, carbon atoms.

The physiologically compatible acid addition salts are derived from known inorganic and organic acids, such as, e.g., hydrochloric acid, sulfuric acid, hydrobromic acid, citric acid, maleic acid, fumaric acid or tartaric acid.

The compounds of general formula I and their pharmaceutically acceptable acid addition salts exhibit pharmacological actions, especially central dopaminergic effectiveness, and therefore it is a further object of this invention to provide pharmaceutical agents, comprising compounds of formula I and a pharmaceutically acceptable excipient.

Upon further study of the specification and appended claims, further objects and advantages of this invention will become apparent to those skilled in the art.

The dopaminergic agonistic action was determined using the methods described by Horowski for automatic registration of stereotypes on rats (Arzneim. Forsch. 12, 2281-2286, 1978): immediately after intraperitoneal administration of test substance or vehicle, male Wistar rats (90-120 g) are placed individually in acrylic glass cages. The number of contacts on a steel cup with a central metal rod as a result of the stereotypic chewing, licking and gnawing movements in 60 minutes is recorded by an electrodynamic receiving system placed in front of the head of the animal. The mean value ± SEM of the number of contacts in 60 minutes for the various treatment groups, which number 12 animals each, are calculated and the significance of the difference between the mean values of the various test substance doses in comparison with the control group treated with the vehicle is determined with the help of a simple analysis of variance in connection with the Dunnett test. These results are summarized in Table 1:

TABLE 1

Dopaminergic agonistic action of compounds of this invention

| mg/kg administered | Number of stereotypic contacts/60 min (mean + SEM) | |
|---|---|---|
| | Compound 1[a] | Compound 2[b] |
| Vehicle control (0.00) | 872 ± 175 | 1336 ± 185 |
| 0.025 | 4736 ± 892* | 2718 ± 563 |
| 0.10 | 6197 ± 929+ | 8566 ± 1483⊤ |
| 0.39 | 11,515 ± 1364+ | 8583 ± 951⊤ |

TABLE 1-continued

| Dopaminergic agonistic action of compounds of this invention | | |
|---|---|---|
| | Number of stereotypic contacts/60 min (mean + SEM) | |
| mg/kg administered | Compound 1[a] | Compound 2[b] |
| 1.56 | 8945 ± 1434+ | 8061 ± 899+ |
| 6.25 | | 7899 ± 1055+ |

[a] 1,1-diethyl-3-(2-methyl-6-n-propyl-8α-ergolinyl)urea
[b] 3-(6-allyl-2-methyl-8α-ergolinyl)-1,1-diethylurea
*$p < 0.05$
+$p < 0.01$ Since the compounds according to the invention are distinguished by dopaminergic agonist action, they are especially suitable for the treatment of diseases and conditions caused by a deficit of dopamine in mammals, especially humans, and especially for the treatment of Parkinson's disease.

The pharmacologically active compounds of this invention can be processed in accordance with conventional methods of galenic pharmacy to produce medicinal agents for administration to patients, e.g., mammals including humans.

To use the compounds according to the invention as pharmaceutical agents they are put into the form of a pharmaceutical preparation, which, besides the active ingredient for enteral or parenteral application, contains organic or inorganic inert vehicles, such as, for example, water, gelatin, gum arabic, lactose, starch, magnesium stearate, talc, vegetable oils, polyalkylene glycols, etc. The pharmaceutical preparations can be present in solid form, for example, as tablets, dragees, suppositories, capsules or in liquid form, for example, as solutions, suspensions or emulsions. Further, they optionally contain auxiliary agents such as preservatives, stabilizing agents, wetting agents or emulsifiers, salts for changing the osmotic pressure or buffers.

Generally, the compounds of this invention are dispensed in unit dosage form comprising 0.001 to 10 mg in a pharmaceutically acceptable carrier per unit dosage.

The dosage of the compounds according to this invention generally is 0.00001 to 0.1 mg/kg/day, preferably 0.0001 to 0.01 when administered to patients, e.g., humans to treat Parkinson's disease analogously to the known agent bromocriptine.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Compounds of this invention may be used instead of, or in conjunction with, conventional compounds for treatment of dopamine-deficit conditions. Thus, for example, the compounds of this invention may be administered in a ratio of 1:10,000, preferably 1:2000, on a daily basis, with the conventional compound, for example, L-Dopa, and administered either simultaneously or sequentially with the conventional compound.

The production of the compounds of formula I according to the invention can performed according to methods known in the art.

For example, the compounds of formula I are synthesized as follows:

a) a compound of formula II

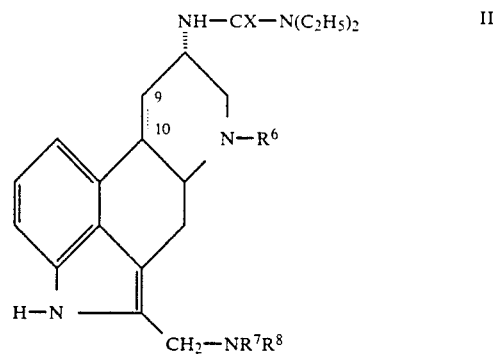

in which $R^6$, X and $C_9$—$C_{10}$ have the above meaning and $R^7$ and $R^8$ each independently are $C_{1-6}$ or together with the nitrogen atom mean a 5-6-membered saturated heterocycle, which optionally can be interrupted by an oxygen atom, is oxidized to the aldehyde of formula Ia

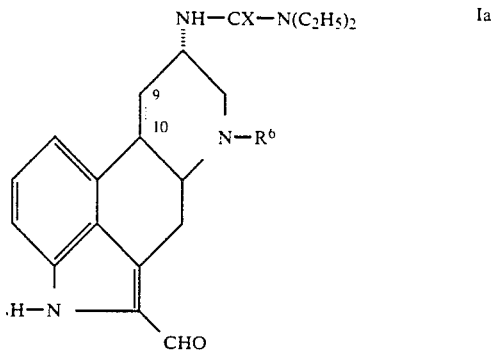

in which $R^6$, X and $C_9$—$C_{10}$ have the above meanings;

b) the quaternary salt of formula IIa

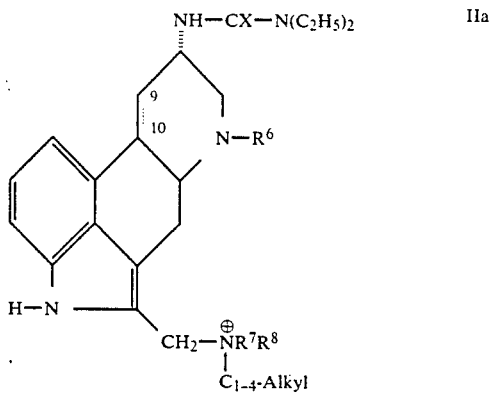

in which $R^6$, $R^7$, $R^8$, x and $C$—$C_{10}$ have the above meanings, is reduced to a compound of formula I, in which $R^2$ is methyl or is reacted with a nucleophilic anion and optionally, in a compound of formula I thus obtained, in which $R^2$ is $CH_2$—O—benzyl, the benzyl group is cleaved off and the $CH_2OH$ group thus obtained is optionally esterified or oxidized to the aldehyde of formula IA;

c) a compound of formula Ia

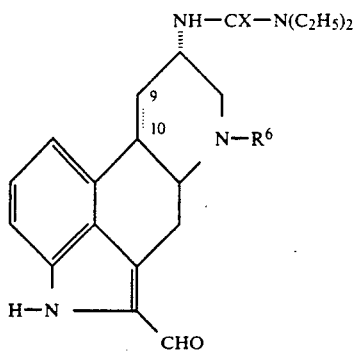

Ia in which $R^6$, X and $C_9$—$C_{10}$ have the above meanings, is either i) reacted with a Wittig reagent to a compound of formula I, in which $R^2$ represents a $C_{2\text{-}10}$ alkenyl radical optionally substituted with halogen, or ii) converted into a compound of formula I with $R^2$ meaning $CH(OH)R^5$, and optionally is then converted into a compound of formula I, in which $R^2$ stands for $C_{2\text{-}10}$ alkenyl or $C_{2\text{-}10}$ alkyl, or the hydroxyl group is esterified or oxidized to the ketone and optionally then the compound of formula Ib thus obtained

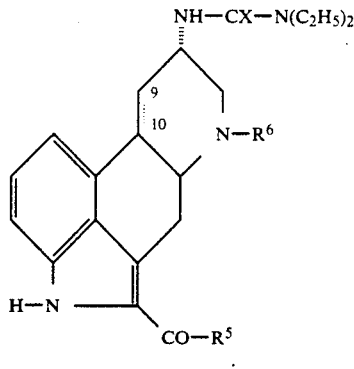

Ib in which $R^6$, X, $R^5$ and $C_9$—$C_{10}$ have the above meanings, analogously to ii), is converted into $CR^{12}(OH)R^5$, in which $R^{12}$ has the meaning of $C_{1\text{-}9}$ alkyl and optionally is then converted into a compound of formula I, in which $R^2$ stands for $C_{2\text{-}10}$ alkenyl or $C_{2\text{-}10}$ alkyl, or the hydroxyl group is esterified, and optionally then the unsaturated compounds obtained according to i) or ii) are reduced to compounds of formula I, in which $R^2$ stands for $C_{2\text{-}10}$ alkyl;

d) a compound of formula IV

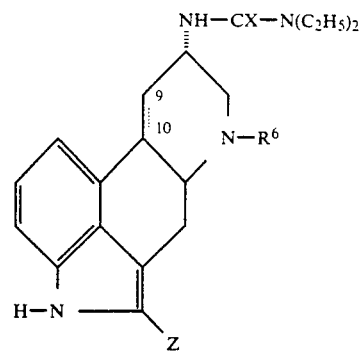

IV in which $R^6$, X and $C_9$–$C_{10}$ have the above meaning, and Z is halogen or lithium, is alkylated or alkenylated to a compound of formula I, in which $R^2$ stands for $C_{1\text{-}10}$ alkyl or $C_{2\text{-}10}$ alkenyl; or e) a compound of formula V

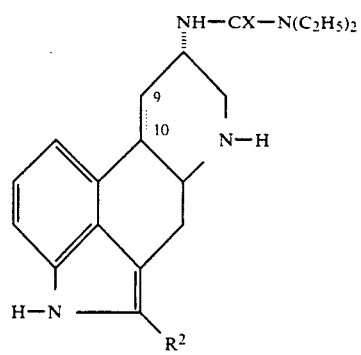

V in which $R^2$, X and $C_9$—$C_{10}$ have the above meanings, is alkylated in the 6 position and then optionally the compounds of formula I with X meaning oxygen obtained according to processes a–e are converted into the thioureas or reduced to the 2,3-double bond or the acid addition salts are formed or the isomers are separated.

The oxidation of the Mannich base of formula II according to process a) can be performed, for example, at temperatures from 0° C. to −40° C. in inert solvents, such as, for example, ethers, with tert-butyl hypochlorite.

Piperidine, morpholine or pyrrolidine, for example, are suitable as 5–6-membered saturated heterocycle —$NR^7R^8$, which optionally can be interrupted by an oxygen atom.

Reaction of the compounds of formulas II and IIa according to process b) can be performed according to the methods described in EP-A-250 357. For example, the 2-position of the ergoline of the quaternary salt of a disubstituted aminoethyl compound can be reduced with sodium borohydride in polar solvents, such as, for example, alcohols to leave the 2-methyl compound, or by use of nucleophilic anions can be substituted to the compounds of formula I in which $R^2$ means $CH_2YR^3$ or $CH_2CHR^9COR^{10}$. The nucleophilic exchange takes place after quaternization of the aminomethyl group with $C_{1\text{-}4}$ alkyl halides, for example, with methyliodide, in an inert solvent such as alcohols, ethers or chlorinated hydrocarbons at room temperature or elevated temperature, and nucleophilic anions, for example, mercaptides, alcoholates and β-dicarbonyl compounds such as malonic ester, acetoacetic acid and acetylacetone can be reacted.

The optional subsequent conversion of the $CH_2$—O—benzyl group to the $CH_2OH$ group can take place, for example, by cleavage of the benzyl radical, with sodium or lithium in liquid ammonia and an inert solvent such as ether.

Esterification of the hydroxyl group can take place, in each case, according to the usual methods, for example, by reaction with acid hydrides in the presence of the corresponding aliphatic carboxylic acid and its alkali salts in protic solvents or by reaction with acid chlorides in the presence of organic bases.

Conversion of the 2-formyl compounds of formula Ia into compounds of formula I, in which $R^2$ means an optionally halogen-substituted $C_{2-10}$ alkenyl radical, can take place in a Wittig reaction, for example, by a compound of formula Ia being reacted with a usual Wittig reagent such as, for example, triphenylphosphine, tetrahalomethane, alkyltriphenylphosphonium halide or haloalkyltriphenylphosphinotetrafluoroborate, optionally after introduction of conventional protecting groups as a proton donor. The Wittig reaction can be performed in polar solvents such as cyclic or acyclic ethers, chlorinated hydrocarbons, dimethylformamide or dimethyl sulfoxide at temperatures of $-50°$ C. to the boiling temperature of the reaction mixture, and strong bases such as alkali alcoholates, lithium organyl and the like are added for the production of the ylene.

If the compounds of formula I, in which $R^2$ means $CR^{12}(OH)R^5$, are produced according to process c), the production can take place, for example, by Grignardizing or lithium alkylation. The Grignardizing can take place with the usual Grignard reagents such as alkyl magnesium halides in an aprotic solvent such as cyclic and acyclic ethers at low temperatures ($-70°$ C. to $0°$ C.). The reaction with alkyl lithium takes place under similar conditions. Esterification of the hydroxyl group can be performed according to the processes described above.

Oxidation to a 2—CHO according to process b) or to a 2—CO—$R^5$ compound according to process c) can take place in each case analogously to the process described in R. A. Jones et al. Synthetic Communications 16, 1799 (1986), for example, with manganese dioxide in inert solvents at room temperature.

The optional subsequent introduction of the double bond can be carried out using the usual dehydrating methods, such as with sulfonates or acetates, such as methane sulfonic acid chloride in polar solvents, such as ethers in the presence of a base, and optionally with heating.

If substituent $R^2$ contains an exocyclic double bond, the latter can be reduced in the usual way to the corresponding alkyl derivative. For example, the reduction can take place catalytically with palladium/carbon or Raney nickel at room temperature in an aliphatic alcohol or the reduction can be performed with sodium in liquid ammonia in an inert solvent such as cyclic and acyclic ethers in the presence of a proton donor such as aliphatic alcohols.

If substituent $R^2$ contains a 2-hydroxyl group, the latter can be reduced, for example, with $NaBH_4$ in glacial acetic acid to the corresponding 2-alkyl derivative.

Process d) can take place, for example, according to the methods described in EP-A-160 842 such as reaction of 2-lithium ergolines with an electrophilic reagent or reaction of 2-halogen ergolines in the presence of a palladium catalyst and a base.

Process e) describes 6-alkylation of ergolines substituted in the 2 position with $R^2$. This synthesis method can take place, for example, according to A. Cerny et al. Coll. Chech. Chem. Comm. 49, 2828 (1984), by the 6-cyanoergoline being reduced to the 6-H compound and the latter then being alkylated with the corresponding halides or according to the process described in EP-21206.

Conversion of the urea derivatives into the thiourea derivatives can take place, for example, according to the process described in EP-A-217 730, which corresponds to U.S. Pat. No. 4,801,714, by reaction with phosphoroxychloride and a thiolizing agent, such as, for example, an alkali metal xanthate. Reduction of the 2,3-double bond can take place, for example, according to the process described in EP-A-286575 with organylsilanes in the presence of an acid, such as trifluoroacetic acid or by sodium borohydride. The compounds of formula I are isolated either as free bases or in the form of their acid addition salts.

For the formation of salts a compound of formula I is dissolved, for example, in methanol or methylene chloride and mixed with a concentrated solution of the desired acid.

The isomer mixtures can be separated according to the usual methods such as, for example, crystallization, chromatography or salt formation into the diastereomers or E/Z isomers.

It is a further object of this invention to provide the compounds of formula II, IIa, Ia, Ib, IV and V, which are useful as valuable intermediate products for the production of pharmacologically effective compounds. The conversion of the intermediate products into effective substances takes place according to the process described above.

The compounds of formula V can be obtained by a coupling reaction of 2-haloergolines with an organometallic compound with metal catalysis. Bromine and iodine derivatives are preferred, which in an inert solvent such as cyclic and acyclic ethers, hydrocarbons or dimethylformamide in the presence of a nickel or palladium catalyst, are reacted with an organometallic compound at temperatures up to the boiling point of the reaction mixture. Suitable as organometallic compounds are $C_{1-10}$ alkyl and $C_{2-10}$ alkenyl Me-$X_n$ derivatives, in which Me is zinc, magnesium, tin or boron, X is halogen, preferably chlorine or bromine, $C_{1-4}$ alkyl or hydroxy and n can be 1–3, depending on the valence of the metal atom.

1,3-diphenylphosphinopropane nickel(II) chloride, for example, can be used as nickel catalyst. Bis-tri-o-tolylphosphine palladium(II) chloride, bis-triphenylphosphine palladium(II) chloride, tetrakis-triphenylphosphine palladium(II) chloride and 1,1'-bis-diphenylphosphinoferrocene palladium(II) chloride can be used as palladium catalysts.

Insofar as the production of the initial compounds is not described, they are known or can be produced analogously to known compounds or processes described here.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German applications P 38 24 661.9 and P 39 17 268.6, are hereby incorporated by reference.

The following examples are to explain the process according to the invention:

EXAMPLES

Production of the initial compounds

1. General procedure for the Mannich reaction of 3-(6-alkyl-8α-ergolinyl)-1,1-diethylureas.

30 mmol of ergoline, 24.0 g (0.19 mol) of morpholine hydrochloride, 4.5 g (0.15 mol) of paraformaldehyde and 220 ml of dry dimethylformamide are combined in the indicated sequence and the mixture is stirred for 30 minutes in an oil bath preheated to 100° C. For working up, the reaction mixture is poured onto ice, made alkaline with 25% $NH_3$ solution and extracted with toluene. After drying on $Na_2SO_4$ and removal of the toluene in a vacuum, the resulting product is dissolved in 100 ml of trifluoroacetic acid and stirred for 30 minutes at 60° C. Then the reaction mixture is poured onto ice and made alkaline with 25% $NH_3$ solution. After extraction with dichloromethane, drying on $Na_2SO_4$ and removal of the solvent in a vacuum, a dark oil is obtained, which is purified by chromatography.

The following compounds were produced:

1,1-diethyl-3-(2-morpholinomethyl-6-n-propyl-8α-ergolinyl)-urea

Yield after chromatography ($SiO_2$, dichloromethane/methanol 97:3): 78–89% $[α]_D +11.3°$ (c=0.5 in chloroform).

1,1-diethyl-3-(2-morpholinomethyl-6-n-propyl-8α-ergolinyl)-urea, L-hydrogen tartrate Yield: 84% (crystalline), $[α]_D +1.6°$ (c=0.5 in methanol).

1,1-diethyl-3-(2-morpholinomethyl-6-cyclopropylmethyl-8α-ergolinyl)-urea

Yield after chromatography ($SiO_2$, dichloromethane/methanol 99:1–97:3): 66%, $[α]_D -0.8°$ (c=0.5 in chloroform).

3-(6-allyl-2-morpholinomethyl-8α-ergolinyl)-1,1-diethylurea

Yield after chromatography ($SiO_2$, dichloromethane/methanol (97:3): 71–97% (36–59% crystalline), $[α]_D +2.4°$ (c=0.5 in chloroform).

1,1-diethyl-3-(6-ethyl-2-morpholinomethyl-8α-ergolinyl)-urea

Yield after chromatography ($SiO_2$, dichloromethane/methanol 99:1–95:5): 81% (46% crystalline), $[α]_D +4.0°$ (c=0.5 in chloroform).

3-(6-cyano-9,10-didehydro-2-morpholinomethyl-8α-ergolinyl)-1,1-diethylurea

Yield after chromatography (ethyl acetate/methanol 98:2–96:4): 46% (24% crystalline from ethyl acetate), $[α]_D +301.6°$ (c=0.5 in chloroform).

2. General procedure for quaternization of the Mannich compound.

10 mmol of ergoline is dissolved in about 200 ml of tetrahydrofuran and mixed with 4.0 ml (65 mmol) of methyliodide. It is allowed to stir for 17–22 hours at room temperature. Then the mixture, from which already after about 4 hours the product begins to precipitate, is cooled in an ice bath and mixed with 100 ml of diisopropyl ether by instillation. After 30 minutes at 0° C. the quaternary salt is suctioned off. The resulting material is used without characterizing for further reactions.

The following compounds are produced:

N-(8α(3,3-diethylureido)-6-n-propyl-2-ergolinyl-methyl)-N-methyl-morpholinium iodide Yield: 70–81%

N-(6-allyl-8α-(3,3-diethylureido)-2-ergolinyl-methyl)-N-methyl-morpholinium iodide Yield: 59–70%

N-(6-cyclopropylmethyl-8α-(3,3-diethylureido)-2-ergolinyl-methyl)-N-methyl-morpholinium iodide Yield: 64–80%

N-(6-ethyl-8α(3,3-diethylureido)-2-ergolinyl-methyl)-N-methyl-morpholinium iodide Yield: 87%

N-6-(cyano-9,10-didehydro-8α(3,3-diethylureido)-2-ergolinyl-methyl)-N-methyl-morpholinium iodide Yield: 82%

3. Bromination of 1,1-diethyl-3-8α-ergolinyl)-urea 3-(2-bromo-8α-ergolinyl)-1,1-diethylurea Production and data, see EP-56358

4. 1,1-diethyl-3-(2-ethyl-8α-ergolinyl)-urea 1.00 g (2.47 mmol) of 3-(2-bromo-8α-ergolinyl)-1,1-diethylurea is dissolved in 10 ml of toluene, mixed with 90 mg (0.12 mmol) of 1,1'-bis(diphenylphosphino)-ferrocene palladium(II) chloride and stirred for 15 minutes at room temperature. Then 5.5 ml of triethylborane (1M solution in tetrahydrofuran) and 2.5 ml of 4N potassium hydroxide solution are added and the mixture is refluxed for 4 hours. The reaction mixture is acidified with 2N hydrochloric acid, made alkaline with concentrated ammonia and extracted with dichloromethane. The raw product, obtained after drying of the organic phases (sodium sulfate) and removal of the solvent in a vacuum, is chromatographed on silica gel. (dichloromethane/methanol 98:2). Yield after crystallization (ethyl acetate): 307 mg (35%) $[α]_D +47.6°$ (c=0.5 in chloroform).

5. Reduction of the cyanamide (performed according to the methods known in the literature: A. Cerny et al., Collection Czechoslovak Chem. Commun. 1984, 49, 2828).

The following compounds were produced from the 6-cyano derivatives:

3-(9,10-didehydro-2-methyl-8α-ergolinyl)-1,1-diethylurea 3-(9,10-didehydro-2-methoxymethyl-8α-ergolinyl)-1,1-diethylurea 3-(9,10-didehydro-2-methylthiomethyl-8α-ergolinyl)-1,1-diethylurea 3-(9,10-didehydro-2-hydroxymethyl-8α-ergolinyl)-1,1-diethylurea 3-(9,10-didehydro-2-ethyl-8α-ergolinyl)-1,1-diethylurea 6. 3-(6-cyano-9,10-didehydro-2-methyl-8α-ergolinyl)-1,1-diethylurea Production analogous to example 1.

7. 3-(6-cyano-9,10-didehydro-2-methylthiomethyl-8α-ergolinyl)-1,1-diethylurea

Production analogous to example 2.

8. 3-(6-cyano-9,10-didehydro-2-methoxymethyl-8α-ergolinyl)-1,1-diethylurea

Production analogous to example 4.

9. 3-(6-cyano-9,10-didehydro-2-hydroxymethyl-8α-ergolinyl)-1,1-diethylurea was obtained by reduction of the 2-formyl compound by conventional methods.

10. 3-(6-cyano-9,10-didehydro-2-hydroxyethyl-8α-ergolinyl)-1,1-diethylurea

Production analogous to example 8.

11. 3-(6-cyano-9,10-didehydro-2-ethyl-8α-ergolinyl)-1,1-diethylurea

Production according to example 13.

EXAMPLE 1

General procedure for reduction of the quaternary salt with sodium borohydride 1.00 mmol of ergoline is dissolved in 25 ml of dry ethanol, mixed with 184.6 mg (5.00 mmol) of pulverized $NaBH_4$ and is stirred at room temperature. After the end of the reaction (as determined by TLC), it is poured onto the ice and extracted with dichloromethane. After drying on $Na_2SO_4$ and removal of the solvent in a vacuum, the raw product obtained is purified by chromatography or crystallization.

The following compounds were produced:

3-(6-cyclopropylmethyl-2-methyl-8α-ergolinyl)-1,1-diethylurea

Yield after crystallization (ethyl acetate/diisopropyl ether): 61% $[\alpha]_D - 5.2°$ (c=0.5 in chloroform).

3-(6-allyl-2-methyl-8α-ergolinyl)-1,1-diethylurea

Yield after chromatography ($SiO_2$, dichloromethane/methanol 95:5): 67% (37% crystalline), $[\alpha]_D - 2.0°$ (c=0.5 in chloroform).

1,1-diethyl-3-(6-ethyl-2-methyl-8α-ergolinyl)-urea

Yield after chromatography ($SiO_2$, dichloromethane/methanol 97:3): 33% (13% crystalline), $[\alpha]_D + 3.2°$ (c=0.5 in chloroform).

3-(6-n-propyl-2-methyl-8α-ergolinyl)-1,1-diethylurea

Yield after crystallization (ethyl acetate/diisopropyl ether): 65%, $[\alpha]_D + 34°$ (c=0.5 in pyridine).

EXAMPLE 2

General procedure for reaction of the quaternary salt with sodium methane thiolate 1.00 mmol of ergoline is dissolved in 50 ml of dichloromethane and mixed with 600-800 mg (8.56-11.14 mmol) of $NaSCH_3$. It is stirred for 5-17 hours at room temperature, if necessary more $NaSCH_3$ is added (TLC). For working up it is poured onto ice/$NH_3$ solution and extracted with dichloromethane. After drying on $Na_2SO_4$ and removal of the solvent in a vacuum, the material obtained is further purified by chromatography.

The following compounds were produced:

1,1-diethyl-3-(2-methylthiomethyl-6-n-propyl-8α-ergolinyl)-urea

Yield after chromatography ($SiO_2$, ethyl acetate/methanol 97:3): 43% (34% crystalline), $[\alpha]_D + 12.8°$ (c=0.5 in chloroform).

3-(6-cyclopropylmethyl-2-methylthiomethyl-8α-ergolinyl)-1,1-diethylurea

Yield after chromatography ($SiO_2$, dichloromethane/methanol 97:3): 46% (40% crystalline), $[\alpha]_D - 2.4°$ (c=0.5 in chloroform).

3-(6-allyl-2-methylthiomethyl-8α-ergolinyl)-1,1-diethylurea

Yield after chromatography ($SiO_2$, ethyl acetate/methanol 97:3): 51% (42% crystalline), $[\alpha]_D 0.0°$, (c=0.5 in chloroform).

1,1-diethyl-3-(6-ethyl-2-methylthiomethyl-8α-ergolinyl)-urea

Yield after chromatography ($SiO_2$, dichloromethane/methanol 97:3): 38% (24% crystalline), $[\alpha]_D + 8.1°$ (c=0.5 in chloroform).

EXAMPLE 3

General procedure for reaction of quaternary salt with sodium benzylate 1.17 g (0.05 mol) of sodium in small pieces is dissolved in 40 ml of dry benzyl alcohol with warming. 10 mmol of the quaternary salt is dissolved in the minimal amount of benzyl alcohol (25-50 ml) and slowly instilled into the benzylate solution cooled to room temperature. After completion of the addition, it is allowed to stir for 30 more minutes (TLC). After working up, the reaction solution is chromatographed directly (1.3 kg $SiO_2$, dichloromethane). The benzyl alcohol is eluted with dichloromethane (about 10 l). After addition of 1-3% of methanol to the mobile solvent the product is finally obtained.

The following compounds were produced:

3-(2-benzyloxymethyl-6-n-propyl-8α-ergolinyl)-1,1-diethylurea

Yield: 93%

3-(2-benzyloxymethyl-6-n-propyl-8α-ergolinyl)-1,1-diethylurea, L-hydrogen tartrate Yield: 43% $[\alpha]_D + 12.4°$ (c=0.5 in methanol).

3-(2-benzyloxymethyl-6-cyclopropylmethyl-8α-ergolinyl)-1,1-diethylurea

Yield: 43% (15% crystalline), $[\alpha]_D - 8.2°$ (c=0.5 in chloroform).

3-(6-allyl-2-benzyloxymethyl-8α-ergolinyl)-1,1-diethylurea

Yield: 73% (31% crystalline), $[\alpha]_D - 9.2°$ (c=0.5 in chloroform).

3-(2-benzyloxymethyl-6-ethyl-8α-ergolinyl)-1,1-diethylurea

Yield: 57%

3-(2-benzyloxymethyl-6-ethyl-8α-ergolinyl)-1,1-diethylurea, L-hydrogen tartrate

Yield: 67% $[\alpha]_D + 8.8°$ (c=0.5 in methanol).

EXAMPLE 4

General procedure for the reaction of quaternary salt with sodium methanolate

A solution of 2.0 mmol of quaternary salt in 20 ml of methanol is instilled at 0° C. in a solution of 230 mg (10.0 mmol) of sodium in 20 ml of dry methanol. After completion of the addition, it is stirred for 15 minutes at 0° C. and 30 minutes at room temperature. For working up, it is poured onto ice/$NH_3$ solution and extracted with dichloromethane. The raw product obtained after drying of the organic phases on $Na_2SO_4$ and removal of the solvent in a vacuum is purified by crystallization or chromatography.

The following compounds were produced:

1,1-diethyl-3-(2-methoxymethyl-6-n-propyl-8α-ergolinyl)-urea

Yield after chromatography ($SiO_2$, dichloromethane/methanol 95:5): 44% (28% crystalline), $[\alpha]_D + 5.8°$ (c=0.5 in chloroform).

3-(6-cyclopropylmethyl-2-methoxymethyl-8α-ergolinyl)-1,1-diethylurea

Yield after chromatography ($SiO_2$, dichloromethane/methanol 97:3): 13% (8% crystalline), $[\alpha]_D - 3.6$ (c=0.5 in chloroform).

3-(6-allyl-2-methoxymethyl-8α-ergolinyl)-1,1-diethylurea

Yield after crystallization (ethyl acetate/diisopropyl ether): 23% [α]$_D$−3.0 (c=0.5 in chloroform).

1,1-diethyl-3-(6-ethyl-2-methoxymethyl-8α-ergolinyl)-urea

Yield after crystallization (ethyl acetate/diisopropyl ether): 36%, [α]$_D$−0.9° (c=0.5 in chloroform).

EXAMPLE 5

General procedure for the production of hydroxy methyl compounds from benzyl ethers 2.00 mmol of ergoline is dissolved in 25 ml of dry tetrahydrofuran and instilled in 40 ml of NH$_3$ at −70° C. 180–550 mg (8–24 mmol) of sodium in small pieces is added in portions, and with the addition in each case there is a wait until the last added sodium has reacted. After the feedstock is consumed (TLC), methanol is added and the cooling bath is removed. The solvent remaining after evaporation of the ammonia is removed in a vacuum and the residue is taken up in water. After extraction with dichloromethane, drying of the organic phases on Na$_2$SO$_4$ and removal of the solvent in vacuum the raw product is obtained which is further purified by crystallization or chromatography.

The following compounds were produced:

1,1-diethyl-3-(2-hydroxymethyl-6-n-propyl-8α-ergolinyl)-urea

Yield after chromatography (dichloromethane/methanol 96:4): 88% (58% crystalline from ethyl acetate/diisopropyl ether), [α]$_D$+14.2° (c=0.5 in chloroform).

3-(6-allyl-2-hydroxymethyl-8α-ergolinyl)-1,1-diethylurea

Yield after chromatography (dichloromethane/methanol 97:3): 61% (36% crystalline from ethyl acetate/diisopropyl ether), [α]$_D$+3.4° (c=0.5 in chloroform).

Further, 18% of the 3-(6-allyl-2-methyl-8α-ergolinyl)-1,1-diethylurea was isolated.

1,1-diethyl-3-(6-ethyl-2-hydroxymethyl-8α-ergolinyl)-urea

Yield after chromatography (dichloromethane/methanol 97:3 and 90:10) 69% (36% crystalline from ethyl acetate/diisopropyl ether), [α]$_D$+9.8° (c=0.5 in chloroform).

3-(6-cyclopropylmethyl-2-hydroxymethyl-8α-ergolinyl)-1,1-diethylurea

Yield after chromatography (dichloromethane/methanol 95:5) 44% (27% crystalline from ethyl acetate/diisopropyl ether), [α]$_D$−0.4° (c=0.5 in chloroform).

EXAMPLE 6

General procedure for the acylation of the 2-hydroxy methyl ergoline 1.0 mmol of ergoline is dissolved in 10 ml of glacial acetic acid. 5 ml (0.05 mol) of acetic anhydride and 0.8 g (0.01 mol) of anhydrous sodium acetate are added and allowed to stir overnight at room temperature. For working up, ice is added, it is stirred for 30 minutes and mixed with NH$_3$ solution. After extraction with dichloromethane, drying of the organic phases on Na$_2$SO$_4$ and removal of the solvent in a vacuum, the raw product is obtained which is further purified by crystallization or chromatography.

The following compounds were produced:

3-(2-acetoxymethyl-6-n-propyl-8α-ergolinyl)-1,1-diethylurea

Yield after crystallization: 34% (from ethyl acetate/diisopropyl ether), [α]$_D$+3.2° (c=0.5 in chloroform).

3-(2-acetoxymethyl-6-cyclopropylmethyl-8α-ergolinyl)-1,1-diethylurea

Yield after crystallization: 69% (from ethyl acetate/diisopropyl ether), [α]$_D$−5.6° (c=0.5 in chloroform).

3-(2-acetoxymethyl-6-ethyl-8α-ergolinyl)-1,1-diethylurea

Yield after chromatography (dichloromethane/methanol 95:5) 69% (48% crystalline from ethyl acetate); [α]$_D$−2.3° (c=0.5 in chloroform).

3-(2-acetoxymethyl-9,10-didehydro-6-n-propyl-8α-ergolinyl)-1,1-diethylurea

EXAMPLE 7

3-(2-Acetoxymethyl-6-allyl-8α-ergolinyl)-1,1-diethylurea 213.6 mg (0.54 mmol) of 3-(6-allyl-2-hydroxymethyl-8α-ergolinyl)-1,1-diethylurea is dissolved in 5 ml of pyridine and mixed with 10 ml (0.11 mol) of acetic anhydride. After stirring for 2 hours at room temperature, the reaction mixture is added to ice, stirred for 1 hour and worked up in the way indicated above.

Yield after crystallization: 64% (from ethyl acetate/diisopropyl ether), [α]$_D$−7.2° (c=0.5 in chloroform).

EXAMPLE 8

General procedure for reaction of 2-formyl ergolines with methyllithium 5.00 mmol of ergoline is dissolved in 150 ml of dry tetrahydrofuran and cooled to −65° C. 10–15 mmol of methyllithium (1.6M solution in ether) in 5–7 portions is added. After the last addition, it is allowed to thaw and stirred for 30 minutes more at room temperature. The course of the reaction is followed by thin-layer chromatography. For working up, it is poured onto ice, made alkaline with 25% NH$_3$ solution and extracted with ethyl acetate. The raw product obtained after removal of the solvent is chromatographed.

The following compounds were produced:

1,1-diethyl-3-[2-(1-hydroxyethyl)-6-n-propyl-8α-ergolinyl]-urea (diastereomer mixture)

Yield after chromatography (ethyl acetate/methanol 97:3 to 95:5): 66% (78% rel. to conversion).

3-(6-allyl-2-(1-hydroxyethyl-8α-ergolinyl)-1,1-diethylurea

Yield after chromatography (dichloromethane/methanol 97:3): 28% (diastereomer mixture), (the nonpolar diastereomer was obtained pure with chromatography and crystallized from ethyl acetate/diisopropyl ether. The indicated data relate to this isomer). [α]$_D$ −42.8° (c=0.5 in chloroform).

1,1-diethyl-3-[6-ethyl-2-(1-hydroxyethyl)-8α-ergolinyl]-urea (diastereomer mixture)

Yield after chromatography (ethyl acetate/methanol 95:5 to 90:10) 74% (67% crystalline from ethyl acetate/diisopropyl ether).

(−)-3-(6-cyclopropylmethyl-2-(1-hydroxyethyl)-8α-ergolinyl)-1,1-diethylurea

[α]$_D$ −13.6° (c=0.5 in chloroform), (nonpolar isomer) and (+)-3-(6-cyclopropylmethyl-2-(1-hydroxyethyl)-8α-ergolinyl)-1,1-diethylurea

[α]$_D$ +16.7° (c=0.5 in chloroform), (polar isomer)

Total yield after chromatography (ethyl acetate/methanol 97:3 and 95:5): 50% (66% rel. to conversion)

1,1-diethyl-3-(2-(1-hydroxy-1-methyl-ethyl)-6-N-propyl-8α-ergolinyl)-urea

Yield after chromatography (dichloromethane/methanol 98:2): 73% (47% crystalline from ethyl acetate), $[\alpha]_D$ +23.0° (c=0.5 in chloroform).

EXAMPLE 9

Reactions with Grignard reagents a. 1.28 g (3.2 mmol) of 1,1-diethyl-3-(6-n-propyl-2-formyl-8α-ergolinyl)-urea was reacted with 20 mmol of ethyl magnesium bromide (10 ml of 2M solution in ether) as indicated above. The raw product was first chromatographed on 2 sequentially connected prepacked columns C (Merck company) (ethyl acetate/methanol 97:3). In this case the polar diastereomer was isolated pure in 36% yield.

1,1-diethyl-3-[2-(1-hydroxy-n-propyl)-6-n-propyl-8α-ergolinyl]-urea $[\alpha]_D$ +26.1° (c=0.5 in chloroform), (polar isomer)

The resulting mixed fractions were chromatographed again (dichloromethane/methanol 98:2), and the nonpolar diastereomer was obtained pure in 18% yield.

1,1-diethyl-3-[2-(1-hydroxy-n-propyl)-6-n-propyl-8α-ergolinyl]-urea $[\alpha]_D$ +6.2° (c=0.5 in chloroform), (nonpolar isomer)

Further, 21% of mixed fraction and 11% of feedstock were obtained. Total yield: 74% (82% rel. to conversion).

b. 1.70 g (4.3 mmol) of 1,1-diethyl-3-(6-n-propyl-2-formyl-8α-ergolinyl)-urea was reacted with 43 mmol of n-pentyl-magnesium bromide (10 ml of 2M solution in ether) as indicated above.

1,1-diethyl-3-[2-1-hydroxy-n-hexyl)-6-n-propyl-8α-ergolinyl]-urea (diastereomer mixture)

Yield after chromatography (dichloromethane/methanol 97:3): 25%

EXAMPLE 10

General procedure for production of 2-alkenyl ergolines by elimination of the 2-hydroxyalkyl compounds 1.00 mmol of ergoline is dissolved in 40 ml of tetrahydrofuran p.a. [pro analysi, for analysis] and mixed with 1.4 ml (10 mmol) of triethylamine. After addition of 0.8 ml (10 mmol) of methanesulfonic acid chloride, it is stirred for 30 more minutes at room temperature (TLC after 5 minutes). Then the mixture is poured onto ice, made alkaline with 25% NH₃ solution and extracted with ethyl acetate. The raw product obtained after evaporation of the solvent in a vacuum is chromatographed.

The following compounds were produced:

1,1-diethyl-3-(6-n-propyl-2-vinyl-8α-ergolinyl)-urea

Yield after chromatography (dichloromethane/methanol 97:3): 47% (11% crystalline from ethyl acetate/methanol), $[\alpha]_D$ +44.0° (c=0.5 in chloroform).

1,1-diethyl-3-(6-ethyl-2-vinyl-8α-ergolinyl)-urea

Yield after chromatography (ethyl acetate/methanol 97:3): 41% (24% crystalline from ethyl acetate/diisopropyl ether), $[\alpha]_D$ +34.2° (c=0.5 in chloroform).

3-(6-allyl-2-vinyl-8α-ergolinyl)-1,1-diethylurea

Yield after chromatography (aluminum oxide/ethyl acetate): 53% (31% crystalline from ethyl acetate/diisopropyl ether), $[\alpha]_D$ +3.3° (c=0.5 in chloroform).

3-(6-cyclopropylmethyl-2-vinyl-8α-ergolinyl)-1,1-diethylurea

Yield after chromatography (aluminum oxide/ethyl acetate): 46% (24% crystalline from ethyl acetate/diisopropyl ether), $[\alpha]_D$ +20.3° (c=0.5 in chloroform).

1,1-diethyl-3-(2-isopropenyl-6-n-propyl-8α-ergolinyl)-urea

Yield after crystallization (ethyl acetate/diisopropyl ether): 46% $[\alpha]_D$ +79.0° (c=0.5 in chloroform).

1,1-diethyl-3-(9,10-didehydro-6-n-propyl-2-vinyl-8α-ergolinyl)-urea

Yield 59%, $[\alpha]_D$ +355° (c=0.5 in chloroform).

EXAMPLE 11

Production of the 2-alkenyl ergolines by Wittig reaction 1.58 g (14 mmol) of potassium tert-butanolate was added in three portions in 2-3 minute intervals to a suspension of 5.35 g (14 mmol) of fluoromethyl-triphenyl-phosphine-tetrafluoroborate (Burton, D. J., Wiemers, D. M., J. Fluor. Chem. 27, 85 (1984)) in 120 ml of dry dioxane was instilled. It was allowed to stir for 30 minutes at room temperature and then a solution of 560 mg (1.4 mmol) of 1,1-diethyl-3-(2-formyl-6-n-propyl-8α-ergolinyl)-urea in 15 ml of dioxane was instilled. After 30 minutes (TLC), the batch was poured onto ice and a pH of 3 was padjusted with solid citric acid. It was extracted with ethyl acetate and the organic phase was washed with 2N citric acid. The combined aqueous phases were made alkaline with 25% NH₃ solution with cooling and extracted with dichloromethane. These organic phases were washed with water, dried on MgSO₄ and the solvent was removed in a vacuum. After chromatography (prepacked columns C; Merck company, diisopropyl ether/methanol 95:5) a total yield of 279 mg (48%) of fluorovinyl compound was obtained. By crystallization of the individual fractions, both isomers were obtained pure.

(E)-1,1-diethyl-3-[2-(2-fluoroethylenyl)-6-n-propyl-8α-ergolinyl-urea and (Z)-1,1-diethyl-3-[2-(2-fluoroethylenyl)-6-n-propyl-8α-ergolinyl-urea

EXAMPLE 12

Reduction of 2-alkenyl ergolines

About 15 ml of ammonia is mixed with 345 mg (15 mmol) of sodium at −65° C. and stirred for 5 minutes at this temperature. A solution of 1.00 mmol of ergoline in 25 ml of dry tetrahydrofuran is quickly instilled, and the dark blue solution is decolored after half the addition. After 15 minutes, 0.2 ml of ethanol each is added three times within 5 minutes. Then it is stirred for 10 minutes more at −65° C. and then the reaction is terminated by addition of 15 ml of ethanol and 15 ml of water. The ammonia is allowed to evaporate, it is added to ice and extracted with dichloromethane. The raw product obtained after removal of the solvent in a vacuum is chromatographed or directly crystallized.

The following compounds were produced:

3-(6-allyl-2-ethyl-8α-ergolinyl)-1,1-diethylurea

Yield after chromatography (dichloromethane/methanol 98:2 and 97:3): 76% (27% crystalline from ethyl acetate/diisopropyl ether), $[\alpha]_D$ +2.9° (c=0.5 in chloroform).

1,1-diethyl-3-(2,6-diethyl-8α-ergolinyl)-urea

Yield after chromatography (ethyl acetate/methanol 97:3):85% (40% crystalline from ethyl acetate), $[\alpha]_D$ +6.2 (c=0.5 in chloroform).

EXAMPLE 13

Reduction of the 2-hydroxyalkyl ergolines 2.00 mmol of ergoline is dissolved in 25 ml of glacial acetic acid and 1.0 g (26.4 mmol) of sodium borohydride (half tablets) is added under argon. After the end of the reaction (TLC), it is poured onto ice, made alkaline with 25% NH$_3$ with cooling and extracted with dichloromethane. The raw product obtained after removal of the solvent in a vacuum is chromatographed or directly crystallized.

The following compounds were produced:

3-(6-cyclopropylmethyl-2-ethyl-8α-ergolinyl)-1,1-diethylurea

Yield after chromatography (ethyl acetate/methanol 97:3): 65% (56% crystalline from ethyl acetate/diisopropyl ether), $[\alpha]_D$ −0.8° (c=0.5 in chloroform).

1,1-diethyl-3-(2,6-di-n-propyl-8α-ergolinyl)-urea

Yield after chromatography (ethyl acetate/methanol 97:3): 63% (53% crystalline from ethyl acetate/diisopropyl ether), $[\alpha]_D$ +14.4° (c=0.5 in chloroform).

1,1-diethyl-3-(2-n-hexyl-6-n-propyl-8α-ergolinyl)-urea

Yield after chromatography (ethyl acetate/methanol 95:5): 70% (43% crystalline from ethyl acetate/hexane), $[\alpha]_D$ +14.4° (c=0.5 in chloroform).

1,1-diethyl-3-(2-isopropyl-6-n-propyl-8α-ergolinyl)urea

In the reduction with sodium borohydride a mixture of the desired compound and 1,1-diethyl-3-(2-isopropenyl- 6-n-propyl-8α-ergolinyl)-urea) was produced. Therefore the raw mixture was further reduced with Na/NH$_3$ (see example 12). Yield after crystallization (ethyl acetate): 28%, $[\alpha]_D$ +17.6° (c=0.5 in chloroform).

EXAMPLE 14

N-alkylation of 2-alkyl ergolines

The reaction takes place according to the methods known in the literature, e.g., according to EP-21206.

The following compounds were produced:

1,1-diethyl-3-(2-ethyl-6-n-propyl-8α-ergolinyl)-urea

Yield after chromatography: 64% (34% crystalline from tert-butylmethyl ether/hexane), $[\alpha]_D$ +42.8° (c=0.5 in pyridine).

3-(9,10-didehydro-2-methyl-6-n-propyl-8α-ergolinyl)-1,1-diethylurea, yield 63%, $[\alpha]_D$ +284° (c=0.5 in chloroform).

3-(6-allyl-9,10-didehydro-2-methyl-8α-ergolinyl)-1,1-diethylurea, yield 53%, $[\alpha]_D$ +308° (c=0.5 in chloroform).

3-(6-cyclopropylmethyl-9,10-didehydro-2-methyl-8α-ergolinyl)-1,1-diethylurea, yield 42%, $[\alpha]_D$ +293° (c=0.5 in chloroform).

3-(9,10-didehydro-6-ethyl-2-methyl-8α-ergolinyl)-1,1-diethylurea, yield 69%, $[\alpha]_D$ +311° (c=0.5 in chloroform).

3-(9,10-didehydro-2-methoxymethyl-6-n-propyl-8α-ergolinyl)-1,1-diethylurea, yield 26% $[\alpha]_D$ +260° (c 0.5 in chloroform).

3-(9,10-didehydro-2-methylthiomethyl-6-n-propyl-8α-ergolinyl)-1,1-diethylurea, yield 50% as hydrogen tartrate, $[\alpha]_D$ +169° (c=0.5 in pyridine).

3-(9,10-didehydro-2-hydroxymethyl-6-n-propyl-8α-ergolinyl)-1,1-diethylurea 3-(9,10-didehydro-2-ethyl-6-n-propyl-8α-ergolinyl)-1,1-diethylurea, yield 38% $[\alpha]_D$ +287° (c=0.5 in chloroform).

EXAMPLE 15

General procedure for oxidation of 2-hydroxyalkyl ergolines with manganese dioxide, according to, e.g., R. A. Jones et al., Synthetic Communications 16, 1799 (1986)

1.0 mmol of ergoline is dissolved in 20 ml of dichloromethane p.a. [pro analysi, for analysis] and 865 mg (10 mmol) of MNO$_2$ (precipitated actively of Merck company) is added. It is allowed to stir overnight at room temperature, filtered on aluminum oxide/Celite and rewashed well with dichloromethane and ethyl acetate. The pure product is obtained by crystallization or chromatography.

The following compounds were produced:

3-(6-allyl-2-formyl-8α-ergolinyl)-1,1-diethylurea

Yield after chromatography (dichloromethane/methanol 97:3): 94% (65% crystalline from ethyl acetate/diisopropyl ether), $[\alpha]_D$ +21.3° (c=0.5 in chloroform).

3-(6-cyclopropylmethyl-2-formyl-8α-ergolinyl)-1,1-diethylurea

Yield after crystallization: 70% (from ethyl acetate/diisopropyl ether), $[\alpha]_D$ +27.0° (c=0.5 in chloroform).

3-(2-acetyl-6-n-propyl-8α-ergolinyl)-1,1-diethylurea

Yield: 88% (57% crystalline from ethyl acetate), $[\alpha]_D$ +20.3° (c=0.5 in chloroform).

EXAMPLE 16

General procedure for oxidation of the Mannich compounds with tert-butyl hypochloride 10.0 mmol of ergoline is dissolved in 160 ml of tetrahydrofuran p.a., cooled to −40° C. and 1.6–3.2 ml (11.5–23.0 mmol) of triethylamine is added. Then a solution of 1.5 ml (12.3 mmol) of tert-butyl hypochloride in 25 ml of tetrahydrofuran is quickly instilled. After 5 minutes the mixture is checked by thin-layer chromatography. If feedstock can still be detected, more hypochloride is added. Thirty minutes after the last addition (TLC) the batch is poured onto ice, made alkaline with 25% NH$_3$ solution and extracted with ethyl acetate. The raw product obtained after removal of the solvent in a vacuum must be chromatographed.

The following compounds are produced:

1,1-diethyl-3-(2-formyl-6-n-propyl-8α-ergolinyl)urea

Yield after chromatography (ethyl acetate/methanol 98:2 to 95:5): 36–64%

3-(6-allyl-2-formyl-8α-ergolinyl)-1,1-diethylurea

Yield after chromatography (ethyl acetate/methanol 97:3): 32–65%

3-(6-cyclopropylmethyl-2-formyl-8α-ergolinyl)-1,1-diethylurea

Yield after filtration through aluminum oxide act. III (ethyl acetate): 82%

1,1-diethyl-3-(6-ethyl-2-formyl-8α-ergolinyl)-urea

Yield after chromatography (dichloromethane/methanol 97:3): 28–62%, crystallized from ethyl acetate/diisopropyl ether), $[\alpha]_D$ +43.8° (c=0.5 in chloroform).

3-(6-cyano-9,10-didehydro-2-formyl-8α-ergolinyl)-1,1-dicthylurea, yield 63%.

EXAMPLE 17

General procedure for production of thioureas from ureas 0.13 ml of freshly distilled phosphoroxychloride (1.4 mmol) and 0.23 mmol of ergolinylurea are successively dissolved in 5 ml of dichloromethane at −20° C. The mixture is stirred overnight at room temperature, then the volatile portions are carefully removed in a vacuum and the residue is dissolved in 10 ml of acetonitrile. To this is added at room temperature the solution of 205 mg of potassium methylxanthogenate (1.4 mmol) in 20 ml of acetonitrile, it is stirred for 2 hours at room temperature and mixed with ice and concentrated ammonia solution. The mixture is extracted with dichloromethane, the organic phases are chromatographed with sodium sulfate with ethyl acetate and crystallized from ethyl acetate/diisopropyl ether.

The following compounds were produced:

3-(9,10-didehydro-2-ethyl-6-n-propyl-8α-ergolinyl)-diethylthiourea, yield 15%, $[\alpha]_D = +373°$ (0.25% in chloroform)

3-(9,10-didehydro-2-methyl-6-n-propyl-8α-ergolinyl)-diethylthiourea, yield 39%, $[\alpha]_D = +419°$ (0.5% in chloroform)

1,1-diethyl-3-(2,6-di-n-propyl-8α-ergolinyl)thiourea, yield 51%, $[\alpha]_D = +91°$ (0.25% in chloroform)

1,1-diethyl-3-(2-methyl-6-n-propyl-8αa-ergolinyl)thiourea, yield 61%, $[\alpha]_D = +49°$ (0.5% in chloroform)

EXAMPLE 18

1,1-Diethyl-3-(9,10-didehydro-2,3β-dihydro-2β-methyl-6-n-propyl-8αa-ergolinyl)-urea 880 mg of 3-(9,10-didehydro-2-methyl-6-n-propyl-8α-ergolinyl)-1,1-diethylurea (2.3 mmol) is dissolved in 30 ml of trifluoroacetic acid, and 1.48 ml of triethylsilane is added in three equal portions in the space of 5 minutes. It is stirred for 60 minutes, first ice and then 25% ammonia solution with cooling are added and the alkaline solution is shaken out with dichloromethane. The organic phases are dried and concentrated by evaporation. Yield after chromatography 378 mg. By crystallization from ethyl acetate/diisopropyl ether, 106 mg (12% of theory), is obtained $[\alpha]_D = +204°$ (0.5 % in chloroform).

1,1-diethyl-3-(2,3β-dihydro-2-methyl-6-n-propyl-8α-ergolinyl)-urea

Yield 63%

1,1-diethyl-3-(2,3β-dihydro-6-ethyl-2-methyl-8α-ergolinyl)-urea

Yield 34%, $[\alpha]_D = +50°$ (0.5% in chloroform).

1,1-diethyl-3-(2,3β-dihydro-2,6-di-n-propyl-8α-ergolinyl)-urea

Yield 33%, $[\alpha]_D = +63°$ (0.5% in chloroform).

1,1-diethyl-3-(2,3β-dihydro-6-ethyl-2-methyl-8α-ergolinyl)-thiourea

Yield 28%, $[\alpha]_D = +70°$ (0.5% in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I wherein $C_2$—$C_3$ and $C_9$—$C_{10}$ each represent a single or double bond;

X is oxygen or sulfur;

$R^2$ is $C_{1-10}$-alkyl, $C_{2-10}$-alkenyl, halogen-substituted $C_{2-10}$-alkenyl, $CH_2YR^3$, $CR^{12}(OR^4)R^5$, $CH$—$CH$—$R^9$—$COR^{10}$ or $COR^{12}$, wherein Y is oxygen or sulfur, $R^3$ is hydrogen, $C_{1-4}$-alkyl, phenyl, $C_{2-5}$-alkanoyl or phenyl-$C_{1-4}$-alkyl, $R^4$ is hydrogen or $C_{2-5}$-alkanoyl, $R^5$ is $C_{1-9}$-alkyl, $R^9$ is $COCH_3$ or $COO$—$C_{1-4}$-alkyl, $R^{10}$ is $C_{1-4}$-alkyl or $O$—$C_{1-4}$-alkyl, $R^{12}$ is hydrogen or $C_{1-9}$-alkyl; and $R^6$ is $C_{2-10}$-alkyl, $C_{3-10}$-alkenyl or $C_{4-10}$-cycloalkyl-$C_{1-3}$-alkyl, or an acid addition salt, isomer or isomeric mixture thereof, with the provisos that when $C_2$—$C_3$ is a double bond, (a) $R^2$ is $C_{4-10}$-alkyl, $C_{3-10}$-alkenyl, halogen-substituted $C_{2-10}$-alkenyl, $CH_2YR^3$, $CR^{12}(OR^4)R^5$, $CH_2$—$CHR^9$—$COR^{10}$ or $COR^{12}$, and (i) when $R^2$ is $C_{3-6}$-alkenyl, the double bond is not in the 1-position;

(ii) when $R^2$ is $CH_2YR^3$ and Y is O, $R^3$ is not H;

(iii) when $R^2$ is $CR^{12}(OR^4)R^5$ and $R^{12}$ is H and $R^4$ is H, $R^5$ is $C_{5-9}$ alkyl; and (iv) when $R^2$ is $COR^{12}$, $R^{12}$ is $C_{5-9}$-alkyl; or (b) $R^6$ is $C_{5-10}$-alkyl, $C_{3-10}$-alkenyl or $C_{4-10}$-cycloalkyl-$C_{1-3}$-alkyl.

2. A compound of claim 1, wherein $R^6$ is n-propyl.

3. A compound of claim 1, wherein X is O.

4. A compound of claim 1, wherein X is S.

5. A compound of claim 1, wherein $R^2$ is $C_{1-10}$ alkyl.

6. A compound of claim 5, wherein $R^2$ is —$CH_3$, —$CH_2CH_3$, n-propyl or n-hexyl.

7. A compound of claim 5, wherein $R^2$ is $CH_2YR^3$.

8. A compound of claim 7, wherein Y is S and $R^3$ is $CH_3$.

9. A compound of claim 8, wherein Y is O and $R^3$ is $CH_3$.

10. A compound of claim 1, wherein $R^2$ is $C_{2-10}$ alkenyl.

11. A compound of claim 10, wherein $R^2$ is vinyl.

12. A compound of claim 1, wherein $R^2$ is halogen-substituted $C_{2-10}$ alkenyl.

13. A compound of claim 1, wherein $C_2$—$C_3$ is a double bond.

14. A compound of claim 1, wherein $C_2$ $C_3$ is a single bond.

15. A compound of claim 1, wherein $C_9$ $C_{10}$ is a double bond.

16. A compound of claim 1, wherein $C_9$ $C_{10}$ is a single bond.

17. A compound of claim 1, wherein $C_2$ $C_3$ is a double bond, and $R^2$ is $C_{4-10}$-alkyl, $C_{3-10}$-alkenyl, halogen-substituted $C_{2-10}$-alkenyl, $CH_2YR^3$, $CR^{12}(OR^4)R^5$, $CH_2$—$CHR^9$—$COR^{10}$ or $COR^{12}$, with the provisos that
when $R^2$ is $C_{3-6}$-alkenyl, the double bond is not in the 1-position;
when $R^2$ is $CH_2YR^3$ and Y is O, $R^3$ is not H;
when $R^2$ is $CR^{12}(OR^4)R^5$ and $R^{12}$ is H and $R^4$ is H, $R^5$ is $C_{5-9}$ alkyl; and
when $R^2$ is $COR^{12}$, $R^{12}$ is $C_{5-9}$alkyl.

18. A compound of claim 1, wherein $C_2$ $C_3$ is a double bond, and $R^6$ is $C_{3-10}$-alkyl, $C_{3-10}$-alkenyl or $C_{4-10}$-cycloalkyl-$C_{1-3}$-alkyl.

19. A compound of claim 17, wherein $R^6$ is $C_{5-10}$-alkyl, $C_{3-10}$-alkenyl or $C_{4-10}$-cycloalkyl-$C_{1-3}$-alkyl.

20. 3-(6-Cyclopropylmethyl-2-methyl-8α-ergolinyl)-1,1-diethylurea,
3-(6-allyl-2-methyl-8α-ergolinyl)-1,1-diethylurea,
3-(6-allyl-2-methylthiomethyl-8α-ergolinyl)-1,1-diethylurea,
3-(6-allyl-2-methoxymethyl-8α-ergolinyl)-1,1-diethylurea,
1,1-diethyl-3-(6-cyclopropylmethyl-2-vinyl-8α-ergolinyl)-urea,
3-(6-allyl-2-ethyl-8α-ergolinyl)-1,1-diethylurea, and
3-(6-cyclopropylmethyl-2-ethyl-8α-ergolinyl)-1,1-diethylurea, each compound of claim 18.

21. 1,1-Diethyl-3-(2-methylthiomethyl-6-n-propyl-8α-ergolinyl)-urea,
3-(9,10-didehydro-2-methylthiomethyl-6-n-propyl-8α-ergolinyl)-1,1-diethylurea,
1,1-diethyl-3-(6-ethyl-2-methylthiomethyl-8α-ergolinyl)-urea,
3-(2-benzyloxymethyl-6-n-propyl-8α-ergolinyl)-1,1-diethylurea,
1,1-dimethyl-3-(2-methoxymethyl-6-n-propyl-8α-ergolinyl)-urea,
3-(9,10-didehydro-2-methoxymethyl-6-n-propyl-8α-ergolinyl)-1,1-diethylurea,
1,1-diethyl-3-(3-ethyl-2-methoxymethyl-8α-ergolinyl)-urea,
1,1-diethyl-3-(2-acetoxymethyl-6-n-propyl-8α-ergolinyl)-urea,
(E)-1,1-diethyl-3-[2-(2-fluoroethylenyl)-6-n-propyl-8α-ergolinyl]-urea,
(Z)-1,1-diethyl-3-[2-(2-fluoroethylenyl)-6-n-propyl-8α-ergolinyl]-urea, and
1,1-diethyl-3-(2-n-hexyl-6-n-propyl-8α-ergolinyl)-urea, each a compound of claim 17.

22. 1,1-Diethyl-3-(2,3β-dihydro-6-ethyl-2-methyl-8α-ergolinyl)-thiourea,
1,1-diethyl-3-(9,10-didehydro-2,3β-dihydro-2β-methyl-6-n-propyl-8α-ergolinyl)-urea,
1,1-diethyl-3-(2,3β-dihydro-2-methyl-6-n-propyl-8α-ergolinyl)-urea, and
1,1-diethyl-3-(2,3β-dihydro-2,6-di-n-propyl-8α-ergolinyl)-urea, each a compound of claim 14.

23. A pharmaceutical preparation comprising a compound of claim 1 and a pharmaceutically acceptable excipient.

24. A pharmaceutical preparation comprising (a) a compound of formula I $$NH—CX—N(C_2H_5)_2 \quad I$$

wherein
$C_2$ $C_3$ and $C_9$ $C_{10}$ each represent a single or double bond;
X is oxygen or sulfur;
$R^2$ is $C_{1-10}$-alkyl, $C_{2-10}$-alkenyl, halogen-substituted $C_{2-10}$-alkenyl, $CH_2YR^3$, $CR^{12}(OR^4)R^5$, $CH$—$CH$-$R^9$—$COR^{10}$ or $COR^{12}$,
wherein
Y is oxygen or sulfur,
$R^3$ is hydrogen, $C_{1-4}$-alkyl, phenyl, $C_{2-5}$-alkanoyl or phenyl-$C_{1-4}$-alkyl,
$R^4$ is hydrogen or $C_{2-5}$-alkanoyl,
$R^5$ is $C_{1-9}$-alkyl,
$R^9$ is $COCH_3$ or $COO$—$C_{1-4}$-alkyl,
Y $R^{10}$ is $C_{1-4}$-alkyl or O—$C_{1-4}$-alkyl,
$R^{12}$ is hydrogen or $C_{1-9}$-alkyl; and
$R^6$ is $C_{2-10}$-alkyl, $C_{3-10}$-alkenyl or $C_{4-10}$-cycloalkyl-$C_{1-3}$-alkyl,
or an acid addition salt, isomer or isomeric mixture thereof,
(b) L-Dopa, and (c) a pharmaceutically acceptable excipient.

25. A method of treating a condition caused by a deficit of dopamine, comprising administering an amount of a compound of formula I $$NH—CX—N(C_2H_5)_2 \quad I$$

wherein
$C_2$ $C_3$ and $C_9$ $C_{10}$ each represent a single or double bond;
X is oxygen or sulfur;
$R^2$ is $C_{1-10}$-alkyl, $C_{2-10}$-alkenyl, halogen-substituted $C_{2-10}$-alkenyl, $CH_2YR^3$, $CR^{12}(OR^4)R^5$, $CH$—$CH$-$R^9$—$COR^{10}$ or $COR^{12}$,
wherein
Y is oxygen or sulfur, $R^3$ is hydrogen, $C_{1-4}$-alkyl, phenyl, $C_{2-5}$-alkanoyl or phenyl-$C_{1-4}$-alkyl, $R^4$ is hydrogen or $C_{2-5}$-alkanoyl, $R^5$ is $C_{1-9}$-alkyl, $R^9$ is $COCH_3$ or $COO-C_{1-4}$-alkyl, $R^{10}$ is $C_{1-4}$-alkyl or $O-C_{1-4}$-alkyl, $R^{12}$ is hydrogen or $C_{1-9}$-alkyl; and $R^6$ is $C_{2-10}$-alkyl, $C_{3-10}$-alkenyl or $C_{4-10}$-cycloalkyl-$C_{1-3}$-alkyl, or an acid addition salt, isomer or isomeric mixture thereof.

26. A method of claim 25, wherein the condition is Parkinson's disease.

27. A compound of formula IIa

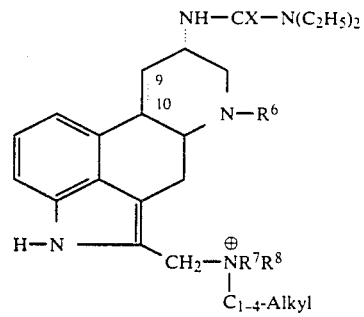

wherein $R^6$ is $C_{2-10}$ alkyl, $C_{3-10}$ alkenyl or $C_{4-10}$ cycloalkyl-$C_{1-3}$-alkyl, X is oxygen or sulfur, $C_9\!-\!C_{10}$ represents a single or double bond, and $R^7$ and $R^8$ each independently are $C_{1-6}$ alkyl or together with the nitrogen atom mean a 5-6-membered saturated heterocycle, which optionally can be interrupted by an oxygen atom, or an acid addition salt, isomer or isomeric mixture thereof.

* * * * *